United States Patent [19]
Romano et al.

[11] Patent Number: 6,093,542
[45] Date of Patent: Jul. 25, 2000

[54] ISOTHERMAL TRANSCRIPTION BASED AMPLIFICATION ASSAY FOR THE DETECTION AND QUANTITATION OF MACROPHAGE DERIVED CHEMOKINE RNA

[75] Inventors: Joseph Romano, Derwood; Ranajit Pal, Gaithersburg, both of Md.; Roxanne Shurtliff, Herndon, Va.

[73] Assignee: Akzo Nobel N.V., Arnhem, Netherlands

[21] Appl. No.: 09/005,165

[22] Filed: Jan. 9, 1998

[51] Int. Cl.[7] .............................. C12Q 1/68; C12P 19/34; C07H 21/04
[52] U.S. Cl. ..................... 435/6; 435/91.3; 536/23.1; 536/24.3; 536/24.33
[58] Field of Search ..................... 435/6, 91.3; 536/23.5, 536/24.3, 24.33

[56] References Cited

U.S. PATENT DOCUMENTS 5,234,809   8/1993   Boom et al. ............................ 435/91.2
5,409,818   4/1995   Davey et al. ........................... 435/91.21
5,554,517   9/1996   Davey et al. ........................... 435/91.21

FOREIGN PATENT DOCUMENTS

WO 96/39521   12/1996   WIPO .
WO 96/40923   12/1996   WIPO .

OTHER PUBLICATIONS

Shaffer et al. Amplification, detection, and automated sequencing of Gibbon interleuin–2 mRNA by Thermus aquaticus DNA polymerase reverse transcription and polymerase chain reaction. Anal. Bioch. vol. 190;292–296, Oct. 1990.

R. Pal et al., *Science*, 278:695–698, 1997.

*Primary Examiner*—John S. Brusca
*Assistant Examiner*—William Sandals
*Attorney, Agent, or Firm*—Michael G. Sullivan; Mary E. Gormley

[57] ABSTRACT

An isothermal transcription based amplification assay for MDC RNA uses primer combinations for sequences within the MDC gene. A quantitative control uses a mutant RNA for comparison.

27 Claims, 1 Drawing Sheet

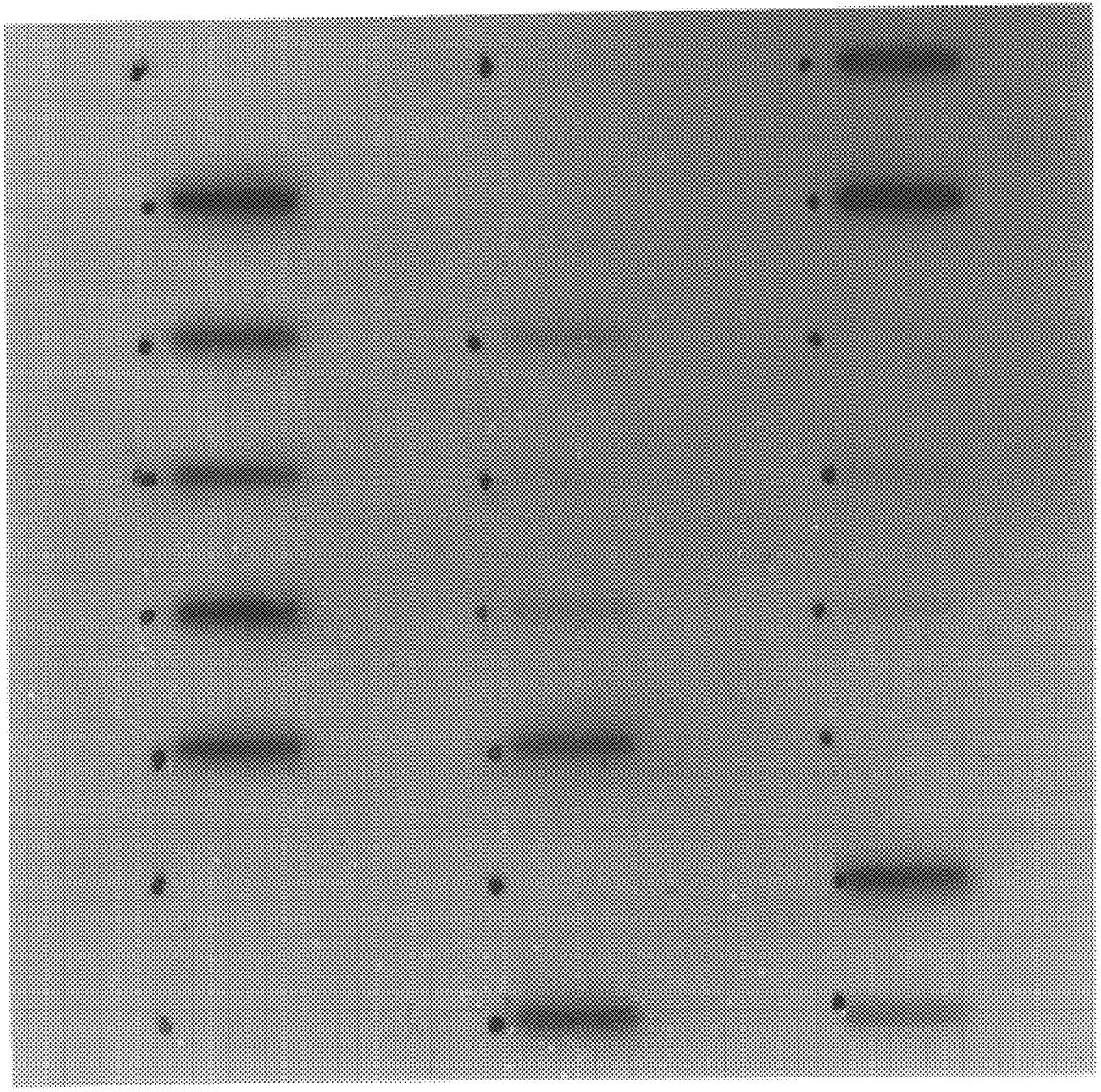

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

AATTCTAATA CGACTCACTA TAGGG                            25

(2) INFORMATION FOR SEQ ID NO:2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:2:

GCAGGGAGGT AGGGCTCCTG AGCC                             24

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

GCAGAGAGTT GGCACAGGCT TCTG                                  24

(2) INFORMATION FOR SEQ ID NO:4:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

AATTCTAATA CGACTCACTA TAGGGGCAGG GAGGTAGGGC TCCTGAGCC        49

(2) INFORMATION FOR SEQ ID NO:5:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

AATTCTAATA CGACTCACTA TAGGGGCAGA GAGTTGGCAC AGGCTTCTG        49

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CCTGCGCGTG GTGAAACACT TCTA                                  24

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

TGGACCTCAG ACTCCTGCCC GA                                    22

(2) INFORMATION FOR SEQ ID NO:8:

```
        (i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:8:

CCGATCCCAG AGTGCCCTGG GTGA                                              24

(2) INFORMATION FOR SEQ ID NO:9:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:9:

AGCCTACTCT GATGACCGTG GCCTTGG                                           27

(2) INFORMATION FOR SEQ ID NO:10:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:10:

AGCCTCACGC AGGTCGTTGA CTCTTGG                                           27
```

ISOTHERMAL TRANSCRIPTION BASED AMPLIFICATION ASSAY FOR THE DETECTION AND QUANTITATION OF MACROPHAGE DERIVED CHEMOKINE RNA

FIELD OF THE INVENTION

The present invention is directed to an isothermal transcription based amplification assay for the detection and quantitation of macrophage derived chemokine (MDC) RNA. The present invention is also directed to oligonucleotides for amplifying MDC RNA.

BACKGROUND OF THE INVENTION

Recently a new CC chemokine has been cloned and characterized, macrophage derived chemokine (MDC). MDC is not closely related to other known chemokines and is produced by macrophages and dendritic cells. It is chemotactic for monocytes, monocyte-derived dendritic cells, and IL-2-activated natural killer cells (Godiska et al, *J. Exp. Med.*, 185(9):1595 (1997)).

It has been clearly demonstrated that certain factors produced by activated CD8+ T cells have been implicated in the suppression of HIV-1 infection (Walker et al., *Science*, 234, 1563, 1986; Brincham et al., *J. Immunol.* 144, 2961, 1990). The production of this suppressor activity correlates with immune status and shows a steady decline in parallel with HIV disease progression (Blackbourn et al., *PNAS* 93, 13125,1996; Mackewicz et al., *J. Clin. Invest.*, 87, 1462, 1991). Although chemokines RANTES, MIP-1a and MIP-1b were shown to be responsible for CD8 suppressor activity (Cocchi et al., *Science* 270, 1811, 1995), these chemokines were not able to explain the full complement of suppressor activity mediated by CD8+ T cells. Recently, Pal et al. have identified a protein from the culture supernatant of HTLV-I transformed CD8+ T lymphocytes which was shown to suppress infection by different phenotypes of HIV-1. This protein was identified to be a variant of MDC as described by Godiska et al. except for the N-terminal amino acid, a difference that is presumably due to variability in $NH_2$ terminal processing between cell types (Pal et al, Science, 278:695 (1997) and U.S. patent application Ser. No. 08/931, 764, which is herein incorporated by reference).

The super family of chemoattractant cytokines (chemokines) and their receptors are involved in inflammation and infection. The chemokines range in size from 68 to 120 amino acids (in the mature form) and can be divided into two major classes based on variations in a shared cysteine motif. The largest group, the C—C, or β chemokines has nearly 20 members identified to date. The C-X-C, or α chemokine branch can be further subdivided into two groups based on structure and function. The largest of these groups contains proteins containing the E-L-R-C-X-C motif and the smaller group is made up of proteins without the E-L-R amino terminal to C-X-C.

The structural classes parallel function to a large extent in that most C-X-C chemokines are chemoattractants for neutrophils but not monocytes, whereas C—C chemokines generally attract monocytes, T-lymphocytes, and in some cases eosinophils, basophils, or mast cells.

The repertoire of known human CC chemokines is expanding rapidly and now includes MIP-1α, MIP-1β, RANTES, I-309, monocyte chemotactic proteins 1, 2, and 3 (MCP-1, -2, -3), MCP-4, eotaxin, HCC-1, thymus and activation regulated chemokine TARC), and Exodus. These proteins are 70–100 amino acids long and have 25–70% identity with each other.

Chemokines act through G-protein coupled receptors, which have a characteristic seven-transmembrane structure. These proteins are structurally related, with amino acid homology high in the transmembrane regions and some intracellular loops. There seems to be less homology at the N- and C-termini, and extracellular loops, which are presumed to be involved in ligand binding (N-terminal) and receptor specific interactions with signaling components.

Five CC chemokine receptors have been described: CCR-1 binds MIP-1α, RANTES, and MCP-3; CCR-2 binds MCP-1, MCP-3, and MCP-4; CCR-3 binds eotaxin, MCP-3, RANTES, and MCP-4; CCR-4 binds MIP-1α, RANTES, and MCP-1; and CCR-5 binds MIP-1α, MIP-1β, and RANTES. Macrophage-tropic strains of HIV appear to require one of the receptors, primarily CCR-5, as a cofactor for infection.

Since MDC contributes a significant portion of the suppressor activity mediated by CDF8+ T cells, identification and quantitation of MDC gene may serve as a prognostic indicator of HIV-1 infection. In particular, it may be necessary to determine whether the level of MDC gene is correlated with virus load in HIV-1 infected individuals. Furthermore, induction of the level of MDC gene in vaccinated subjects may determine the effectiveness of the test vaccine against AIDS. Therefore, establishment of assays to detect and quantitate MDC RNA should serve as an important tool to study pathogenesis in HIV-1 infected patients.

SUMMARY OF THE INVENTION

The present invention provides isothermal transcription based amplification assays for the detection and quantitation of MDC RNA. A preferred embodiment of the detection assay uses one of 4 sets of primers. A preferred embodiment of the quantitation assay uses an internal quantitative control, Q RNA.

Amplification in an isothermal transcription based amplification system is achieved through the coordinated activities of three enzyme activities (reverse transcriptase, RNase H, and RNA polymerase) and two DNA oligonucleotides (referred to herein as primers) specific for the target sequence. The method starts with an RNA template and alternately synthesizes DNA and RNA. Using an RNA template, a primer, and reverse transcriptase, an RNA/DNA hybrid is generated. The RNA is degraded from the hybrid by the RNase H activity. A double stranded DNA is then generated by the reverse transcriptase using another primer, and then the double stranded DNA is used as template for large amounts of RNA synthesis by the RNA polymerase. One of the primers has, in addition to the sequences complementary to the template, additional sequences necessary for generating an RNA polymerase promoter and transcription initiation site which can be used by the RNA polymerase. The single stranded RNA product can be readily detected through the hybridization of an appropriately labeled oligonucleotide DNA probe, with or without an additional probe which can be used to immobilize the amplification product. Detection of an amplification product indicates that the target molecule (RNA) is present in the sample, and detection of specific quantities of amplification product indicate target molecules present in the sample in specific amounts.

The samples used in the methods of the present invention may be various body tissues or cells, or cells cultured in vitro from humans or other animals. In many cases, the sample is peripheral blood mononuclear cells (PBMCs). The level of MDC RNA in the sample correlates with the disease progression and is therefore useful information in the prognosis and/or management of HIV infection.

BRIEF DESCRIPTION OF THE DRAWING

FIG. 1 is an autoradiogram of the products of an isothermal transcription based amplification assay of RNA extracts obtained from PBMCs which have been depleted of CD8+ or CD4+ cells for MDC RNA as described in Example 5.

DETAILED DESCRIPTION OF THE INVENTION

An isothermal transcription based assay is used for the detection and quantitation of MDC RNA. Any isothermal transcription based assay may be used with the primers and probes of the present invention. The isothermal transcription based assay of the present invention is carried out under conditions that can be readily determined by a person of ordinary skill in the art.

The preferred amplification method of the present invention is the isothermal transcription based amplification system referred to as NASBA. The NASBA method is disclosed in U.S. Pat. Nos. 5,409,818 and 5,554,527, which are herein incorporated by reference. NASBA includes the use of T7 RNA polymerase to transcribe multiple copies of RNA from a template including a T7 promoter.

Another technique for the amplification of nucleic acid is the so-called transcription based amplification system (TAS). The TAS method is described in International patent application Ser. No. WO 88/10315. Transcription based amplification techniques usually comprise treating target nucleic acid with two oligonucleotides one of which comprises a promoter sequence, to generate a template including a functional promoter. Multiple copies of RNA are transcribed from said template and can serve as a basis for further amplification.

Other transcription based amplification techniques are described in EP 408295. EP 408295 is primarily concerned with a two-enzyme transcription based amplification method. Transcription based amplification methods, such as the NASBA method described in EP 329822, are usually employed with a set of oligonucleotides, one of which is provided with a promoter sequence that is recognized by an enzyme with DNA dependent RNA polymerase activity such as, for example, T7 polymerase. Several modifications of transcription based techniques are known in the art. These modifications comprise, for example, the use of blocked oligonucleotides (that may be provided with a promoter sequence). These oligos are blocked so as to inhibit an extension reaction proceeding therefrom (U.S. Pat. No. 5,554,516). One or more "promoter-primers" (oligonucleotides provided with a promoter sequence) may be used in transcription based amplification techniques, optionally combined with the use of one or more oligonucleotides that are not provided with a promoter sequence.

The term "oligonucleotide" as used herein refers to a molecule comprised of two or more deoxyribonucleotides or ribonucleotides. Such oligonucleotides may be used as primers and probes.

Of course, based on the sequences of the oligonucleotides of the present invention, analogues of oligonucleotides can also be prepared. Such analogues may constitute alternative structures such as "PNA" (molecules with a peptide-like backbone instead of the phosphate sugar backbone of normal nucleic acid) or the like. It is evident that these alternative structures, representing the sequences of the present invention are likewise part of the present invention.

The term "primer" as used herein refers to an oligonucleotide either naturally occurring (e.g., as a restriction fragment) or produced synthetically, which is capable of acting as a point of initiation of synthesis of a primer extension product which is complementary to a nucleic acid strand (template or target sequence) when placed under suitable conditions (e.g., buffer, salt, temperature and pH) in the presence of nucleotides and an agent for nucleic acid polymerization, such as DNA dependent or RNA dependent polymerase. A primer must be sufficiently long to prime the synthesis of extension products in the presence of an agent for polymerization. A typical primer contains at least 10 nucleotides in length of a sequence substantially complementary or homologous to the target sequence, but somewhat longer primers are preferred. Usually primers contain about 15–26 nucleotides but longer primers may also be employed, especially when the primers contain additional sequences such as a promoter sequence for a particular polymerase.

Normally a set of primers will consist of at least two primers, one "upstream" (P2) and one "downstream" (P1) primer which together define the amplificate (the sequence that will be amplified using said primers). One of the primers is understood to contain, in addition to sequences that will hybridize to the target sequence, sequences which provide promoter activity. Most often the P1 primer will include the promoter sequence.

The term "promoter sequence" defines a region of a nucleic acid sequence that is specifically recognized by an RNA polymerase that binds to a recognized sequence and initiates the process of transcription by which an RNA transcript is produced. In principle, any promoter sequence may be employed for which there is a known and available polymerase that is capable of recognizing the initiation sequence. Known and useful promoters are those that are recognized by certain bacteriophage RNA polymerases such as bacteriophage T3, T7 or SP6. Their function as a primer, e.g., the starting point for an elongation reaction, however, may be blocked, as already mentioned above, or absent in some embodiments of transcription based amplification reactions. A particularly preferred promoter sequence is the sequence of the T7 RNA polymerase promoter:

AATTCTAATACGACTCACTATAGGG      (SEQ ID NO:1)

A preferred embodiment of the present invention is a combination of two oligonucleotides according to the invention, for use as a set in nucleic acid amplification.

One of the oligonucleotides may serve as an "upstream oligonucleotide", i.e., upstream primer, while the second oligonucleotide serves as a "downstream oligonucleotide", i.e., downstream primer, in the amplification reaction.

Preferably, the reverse transcriptase activity is provided by avian myeloblastosis virus (AMV) reverse transcriptase and the RNA polymerase is provided by T7 RNA polymerase.

One of the advantages of an isothermal transcription based amplification method, as compared to other amplification methods such as PCR, is that by being essentially isothermal, it requires few manipulations by the experimenter. However, the absence of a high temperature step does make it somewhat more difficult to find appropriate primers (see below).

The amplification method of the present invention may be applied to extracts of samples comprising nucleic acid, or whole cells or tissues for in situ amplification. The samples may be various body fluids, particularly blood, plasma, and serum, from humans. The samples may also be tissue samples from humans.

If the method is applied to extracts of samples comprising nucleic acids, the sample may be total RNA extracts (such as those described in Chomczynski and Sacchi, *Anal. Biochem.*162:156, 1987) or "Boom" extracts (Boom et al, *J. Clin. Micro.:* 28, No.3, March 1990, p.495–503), which is herein incorporated by reference. The method is preferably applied to "Boom extracts".

The amplificate is detected by hybridization with an appropriately labeled oligonucleotide probe. The label may contain a radioactive moiety, a detectable enzyme, or any other moiety capable of generating a detectable signal, such as a calorimetric, fluorescent, chemiluminescent or electrochemiluminescent (ECL) signal. Blot based hybridization analysis and liquid hybridization based ECL analysis are preferably used, although other analysis systems such as ELGA (enzyme-linked gel assay) and in situ hybridization can also be used.

In one embodiment of the present invention, the amplification products are resolved by agarose gel electrophoresis, then transferred to nylon membranes and hybridized to a probe that is 5'-end labeled with $^{32}P$ using standard methods. The products are then visualized by autoradiography. In a second embodiment of the present invention, the amplification products can be detected using ELGA. In this method a probe that is specific for the amplification reaction product and conjugated at its 5' end with horseradish peroxidase (HRP) is hybridized to the amplification product. The hybridization product is then resolved electrophoretically on a polyacrylamide gel. A calorimetric enzyme reaction allows for the visualization of the reaction product in the gel. A third embodiment of the present invention makes use of electrochemiluminescence chemistry (or ECL). This embodiment uses a biotinylated capture probe immobilized onto the surface of a streptavidin-coated magnetic bead via the biotin-avidin interaction. This system also requires an oligonucleotide detector probe, which can hybridize to an independent region of the amplification product. This detector probe is labeled with Ruthenium, the substance that is responsible for generating an ECL signal.

The quantitative method of the present invention may use one or more internal controls to monitor the efficiency of the extraction process and the amplification assay itself. The detection systems are described in detail in Romano et al, *DNA Technology* 16:89–103 (1996), and van Gemen et al., *J. of Virol. Methods*, 49:157–168 (1994), which are herein incorporated by reference. Methods for internal controls are described in van Gemen et al, *Reviews in Medical Virology*, 5:205–211 (1995), which is herein incorporated by reference.

In a preferred embodiment of the quantitative assay of the present invention, known amounts of in vitro transcribed Q RNA (the internal calibrator described in Example 6) are spiked into the samples prior to RNA extraction, and are thereafter subjected to the same extraction and amplification procedures as the samples themselves. The Q probe is used to detect the Q amplification product and the wild type (wt) probe is used to detect the amplification product of the MDC RNA in the sample. The amount of signal from the Q amplification is then compared to the amount of signal from the wt amplification product to determine the amount of MDC RNA present in the sample.

If the method is to be practiced on fixed preparations for in situ analysis, the method is performed as follows. Samples may include various body fluids or tissue samples. Lymph tissue is a preferred tissue for in situ analysis. The cells are fixed and then permeabilized to optimize permeability of the cell membranes. The fixatives are those standardly used in the art for cell or tissue preparations, such as acetone and methanol, ethanol, formalin, formaldehyde, paraformaldehyde, or Permafix®, and the permeabilization is done by proteinases, such as proteinase K or pepsinogen. The cells are then washed to remove all reagents that might inhibit the transcription based reaction. Permeabilization is done to the point that the cells allow entry of all necessary amplification reaction components, yet retain the targets and amplification products within the cells. In addition, cosolvents such as glycerol or DMSO may be added to optimize the NASBA reaction.

Detection of amplification products may be by direct labelling (with, for instance, biotin or digoxigenin—UTP) or by in situ hybridization with labelled probe. The direct labelling method requires that conditions can be optimized to remove unincorporated label while maintaining the amplification products.

In a particularly preferred embodiment of the present invention, the isothermal transcription based amplification method is used in concert with a particular RNA extraction technique ("Boom extraction", Boom et al, *J. Clin. Micro.:* 28, No.3, March 1990, p.495–503), and ECL detection (electrochemiluminescence). The advantages of the system are those associated with an amplification based assay capable of providing sequence level data. Although some of these same advantages exist for the RT-PCR (i.e., increased sensitivity over ELISA, gene sequence specificity), there are advantages of NASBA for RNA over RT-PCR. These include isothermal amplification, incorporation of reverse transcription into the amplification, application to wider array of specimen types (via Boom extract), and the sensitivity and dynamic range of the ECL detection.

Boom extracts are purified preparations of DNA and RNA. The Boom method is based on the lysing and nuclease inactivating properties of the chaotropic agent guanidinium thiocyanate (GuSCN) together with the nucleic acid binding properties of silica particles or diatoms. By using size fractionated silica particles, nucleic acids, including covalently closed circular, relaxed circular, linear double-stranded DNA, single stranded DNA, tRNA, mRNA, and rRNA, can be purified from a sample in less than one hour and recovered in the original reaction vessel.

A small sample is pipetted into a reaction vessel containing a solid nucleic acid carrier and a GuSCN containing lysis buffer. Lysis of the cells occurs and the released nucleic acids bind to the carrier. The carrier-nucleic acid complexes can be separated by centrifugation. Several wash steps follow and the complexes are then dried. The nucleic acids are eluted in an aqueous low-salt buffer in the initial reaction vessel and used for the amplification reaction.

In a preferred embodiment of the present invention, amplification is achieved in a 20 μL reaction containing 5 μL of the nucleic acid extract material in 10 μL of premix [Tris (40 mM) pH8.5; MgCl$_2$ (12 mM); KCl (70 mM); DTT (5 mM); dNTPs (each) (1 mM); rATP, rUTP, rCTP (2 mM); rGTP (1.5 mM); ITP (0.5 mM); DMSO (15%); P1 and P2, (0.2 μM); Sorbitol (1.5 M)]. This is then added to 5 μL of enzyme mix [BSA (2.1 μg/NASBA); RNase H (0.08 unit/NASBA); T7 RNA Polymerase (32 units/NASBA); and AMV-RT (6.4 units/NASBA)]. (The enzyme mixture must not be vortexed). If the nucleic acid sample decreases (5 μl), then the water volume increases accordingly so that the total volume stays 15 μl when the nucleic acid is added.

The method can be carried out as follows.
1. Mix premix.
2. Add 10 μl of premix to 5 μl of nucleic acid in an EPPENDURF tube.

3. Incubate at 65° C. for 5 minutes.
4. Transfer to 41° C. heat block, incubate for 5 minutes.
5. Add 5 pl of enzyme mix.
6. Mix without vortexing.
7. Incubate at 41° C. for 5 minutes.
8. If the tops of the tubes have condensation from the cooling, they may be spun.
9. Incubate at 41° C. for 90 minutes.
10. Spin down samples and store at −20° C.

In the method of the present invention NASBA primers were designed for the MDC RNA. A total of four primers were designed and synthesized; there were four primer combinations (P1A and P2A; P1A and P2B; P1B and P2A; and P1B and P2B) for the target sequence. The primers and probes are listed on Table 1.

(0.2 μM); Sorbitol (1.5 M)]. This is then added to 5 μL of enzyme mix [BSA (2.1 μg/NASBA); RNase H (0.08 unit/NASBA); T7 RNA Polymerase (32 units/NASBA); and AMV-RT (6.4 units/NASBA)].

The NASBA products were detected using Southern Blot analysis and $^{32}$P-labeled wild type detection probe. The initial analysis indicated that all four primer combinations were functional in NASBA amplification, although pairs AA and BB were better than the others. Primer pair AA was selected for further testing. The results are shown on Table 2.

TABLE 1

MDC Oligonucleotides

Primers

P1A(366-343): 5'GC AGG GAG GTA GGG CTC CTG AGC C3' (SEQ ID NO: 2)

P1B(409-386): 5'GC AGA GAG TTG GCA CAG GCT TCT G3' (SEQ ID NO: 3)

P1A + Pm(366-343): 5'*AAT TCT AAT ACG ACT CAC TAT AGG GGC* AGG GAG GTA GGG CTC CTG AGC C3' (SEQ ID NO: 4)

P1B + Pm(409-386): 5'*AAT TCT AAT ACG ACT CAC TAT AGG GGC* AGA GAG TTG GCA CAG GCT TCT G3' (SEQ ID NO: 5)

P2A(157-180): 5'CCT GCG CGT GGT GAA ACA CTT CTA3' (SEQ ID NO: 6)

P2B(182-203): 5'TGG ACC TCA GAC TCC TGC CCG A3' (SEQ ID NO: 7)

CAPTURE PROBE:248-272: 5'CCG ATC CCA GAG TGC CCT GGG TGA3' (SEQ ID NO: 8)

WT DETECTION PROBE:304-330: 5'AGC CTA CTC TGA TGA CCG TGG CCT TGG3' (SEQ ID NO: 9)

Q DETECTION PROBE: 5' AGC CTC *ACG CAG GTC GTT GAC* TCT TGG 3' (SEQ ID NO: 10)

Pm indicates the T7 RNA polymerase promoter sequence (in italics).

The italicized nucleotides in the Q probe indicate the substitution with regard to the wild type probe.

SEQ ID NOs 4 and 5 comprise the sequence of SEQ ID NOs 2 and 3 operably linked to the T7 promoter sequence (SEQ ID NO:1, shown in italics). This makes sequences 4 and 5 especially suitable for use as downstream primer in a transcription based amplification technique such as NASBA.

EXAMPLE 1

NASBA-Initial Evaluation

The NASBA primers of Table 1 were tested as follows. RNA was extracted by the Boom method and by the method of Chomczynski and Sacchi from the F3B19 cell line. These cells are HTLV-1 transformed CD8+ cells obtained from an HIV-1 positive patient. The primers were used in four different combinations (P1A and P2A, "AA"; P1A and P2B, "AB"; P1B and P2A, "BA"; and P1B and P2B, "BB") in standard NASBA reactions with 5 μL of 1× Boom extract or 5 μL Chomczynski and Sacchi preparation. Negative controls for the amplification contained no nucleic acid sample, i.e., were water only.

Amplification was achieved in a 20 μL reaction containing 5 μL of the nucleic acid extract material in 10 μL of premix [Tris (40 mM) pH8.5; MgCl$_2$ (12 mM); KCl (70 mM); DTT (5 mM); dNTPs (each) (1 mM); rATP, rUTP, rCTP (2 mM); rGTP (1.5 mM); ITP (0.5 mM); DMSO (15%); P1 and P2,

TABLE 2

|    |        | Boom | Total RNA |
|----|--------|------|-----------|
| AA | cells  | +    | +         |
|    | H$_2$O | −    | −         |
| AB | cells  | +/−  | +         |
|    | H$_2$O | −    | −         |
| BA | cells  | +    | +         |
|    | H$_2$O | +/−  | −         |
| BB | cells  | +    | +         |
|    | H$_2$O | −    | −         |

+ denotes a clearly positive result, +/− denotes a weakly positive result, and − denotes a negative result.

EXAMPLE 2

It was desirable to know the sensitivity of the assay using primer set AA. Boom extracts of F3B19 cells were diluted to be equivalent to the number of cells shown in Table 3. The samples were then amplified with primer set AA, slot blotted, and probed with the wild type detection probe. The results (shown on Table 3) indicated that the NASBA based method was very sensitive in detecting MDC RNA.

TABLE 3

| F3B19 cells | AA |
|---|---|
| 5000 | + |
| 500 | + |
| 50 | + |
| 5 | + |
| 0.5 | +/− |
| water | − |

+ denotes a clearly positive result, +/− denotes a weakly positive result, and − denotes a negative result.

EXAMPLE 3

It was desirable to know the specificity of the assay using primer set AA. In vitro transcribed RNA was used as sample, amplified with primer set AA, slot blotted, and probed with the wild type MDC probe. The results indicated that the AA primer set is specific for MDC RNA and does not amplify RANTES, MIP-1α and MIP-1β transcripts (See Table 4).

TABLE 4

| $5 \times 10^5$ copies | AA |
|---|---|
| RANTES WT | − |
| MIP-1α | − |
| MIP-1β | − |
| water | − |
| 500 pg F3B19 | + |
| 5 ng F3B19 | + |

+ denotes a clearly positive result, +/− denotes a weakly positive result, and − denotes a negative result.

EXAMPLE 4

Primer pair AA was then used to determine if MDC RNA is present in PM-1 and HUT-78 cells. PM-1 and HUT-78 cells were previously reported to be negative for MDC RNA by Northern analysis (Pal et al, op. cit.). Both PM-1 and HUT-78 cells were found to be positive for MDC by the NASBA method of the present invention (See Table 5).

TABLE 5

| | cells | AA |
|---|---|---|
| HUT-78 | 5000 | +/− |
| | 500 | +/− |
| | 50 | − |
| PM-1 | 5000 | +/− |
| | 500 | − |
| | 50 | − |
| | water iso | − |
| | water amp | − |
| | 50 pg F3B19 | + |
| | 5 pg F3B19 | + |
| | 50 pg hyb control | + |

+ denotes a clearly positive result, +/− denotes a weakly positive result, and − denotes a negative result.

Two other cell lines were then tested for the presence of MDC RNA. RNA was extracted by the Boom method, amplified using the AA primer pair, and probed with the detection probe. The results shown in Table 6 indicate that the cells lines all contain MDC RNA.

TABLE 6

| | cells | AA |
|---|---|---|
| A2cl5 | 5000 | + |
| | 500 | + |
| | 50 | + |
| | 5 | + |
| | water iso | − |
| | water amp | − |
| | 5 pg F3B19 | + |
| | 500 fg F3B19 | + |
| | 5 pg hyb control | + |
| F3Bcl3 | 5000 | + |
| | 500 | + |
| | 50 | + |
| | 5 | + |
| | water iso | − |
| | water amp | − |
| | 5 pg F3B19 | + |
| | 5 pg hyb control | + |

+ denotes a clearly positive result, +/− denotes a weakly positive result, and − denotes a negative result.

EXAMPLE 5

Samples from HIV-1 infected individuals were also tested in the method of the present invention. PBMCs from nine individuals were treated with DYNAL beads (magnetic beads coated with antibodies to CD4 or CD8) to obtain PBMCs which were depleted for either CD4 or CD8 and then activated with phytohemagglutinin (PHA) (at 5 µg/ml for 48 hours).

Each of the eighteen samples was then Boom extracted and subjected to the amplification method of the present invention using the AA primer pair. The amplification products were then resolved by agarose gel electrophoresis, transferred to nylon membranes and hybridized to the wt detection probe 5'-end labeled with $^{32}P$ using standard methods. The products were then visualized by autoradiography. As shown in FIG. 1, and on Table 6 below, the methods of the present invention were applied successfully to clinical samples. Some patients were positive for MDC RNA in both CD4+ and CD8+ cells (1, 2, 5, 9), some were negative for both (3), and some were positive for either, but not both (4, 6, 7, 8).

TABLE 6

| Sample | Result | Sample | Result | Sample | Result |
|---|---|---|---|---|---|
| neg. control | − | neg. control | − | pos. control | + |
| pos. control | + | (no sample) | | pos. control | + |
| #1, CD8+ cells | + | #4, CD8+ cells | + | #7, CD8+ cells | − |
| #1, CD4+ cells | + | #4, CD4+ cells | − | #7, CD4+ cells | + |
| #2, CD8+ cells | + | #5, CD8+ cells | + | #8, CD8+ cells | + |
| #2, CD4+ cells | + | #5, CD4+ cells | + | #8, CD4+ cells | − |
| #3, CD8+ cells | − | #6, CD8+ cells | − | #9, CD8+ cells | + |
| #3, CD4+ cells | − | #6, CD4+ cells | + | #9, CD4+ cells | + |

+ denotes a clearly positive result, +/− denotes a weakly positive result, and − denotes a negative result.

EXAMPLE 6

A quantitative assay for MDC RNA is developed in the following manner. The cDNA for MDC was cloned and used for the production of in vitro transcribed RNA. This RNA was then diluted and amplified using the AA primer set. The results indicated that the primer set amplified as little as $5 \times 10^1$ copies of the target RNA (data not shown).

The cloned MDC cDNA is then subjected to in vitro mutagenesis to produce the Q version to be used for internal control and quantitation. The Q version of MDC is amplified by the same primer set (AA), but differs from wt MDC by a substitution of 17 nucleotides in the region of the detection probe. The Q RNA therefore would not hybridize to the wt probe, and the wt RNA would not hybridize to the Q probe.

For a quantitative assay, a known amount of Q in vitro transcribed RNA is spiked into the sample and then extracted and amplified along with the sample RNA. After amplification, the products are probed with wt probe and Q probe. The amount of wt RNA present is calculated from the ratio of Q signal to wt signal obtained.

The biggest problem encountered in the development of NASBA assays is the selection of primers. It has often been the case that primers selected from sequence data, and meeting all the known requirements for primers, do not actually function in practice. In addition, in some cases primers have been developed using model systems such as in vitro transcribed RNA, virus stocks, or cells lines with very high expression of the target gene, but those primers were found to be nonfunctional when the target molecule is in a background of clinical samples. The exact mechanism underlying this problem is not understood, but is believed to arise due to the lower temperature of the NASBA reaction, which does not entirely melt secondary structure of the target molecule and/or allows nonspecific binding of primers to background nucleic acids in the sample. It is essential for the application of the NASBA system to clinical samples that the primers be not absorbed by background nucleic acids, but rather be available for specific binding to the target molecule.

The results shown in the present application demonstrate that the primers and probes of the present invention can specifically detect low levels of target molecule, even in the background of clinical samples. In addition, the primers should amplify the Q RNA and the Q and wt probes show appropriate specificity for their cognate targets. Thus, the primers used in the present invention provide unexpectedly good results for the detection and quantitation of MDC RNA.

The present specification provides evidence that the method of the present invention is more sensitive than the prior art methods. Compare the detection of MDC transcript by Northern blot reported by Pal et al (not present in PM1 or HUT-78b cells) with the detection of MDC transcript by the method of the present invention (weakly present in both, see Example 4), Thus, it may be easier to establish correlations between MDC transcript levels and disease state with the method of the present invention due to the increased sensitivity of the amplification based transcript NASBA assay, and the typically larger dynamic range of the quantitative NASBA system.

Interestingly, we have shown that the expression of mRNA encoding other chemokines (e.g., RANTES, MIP-1a, MIP-1b) can be detected in patient PBMC without the need for stimulation by mitogens. Since PBMC samples examined to date for MDC indicate the need for preliminary stimulation, it follows that the expression of different chemokine genes is not regulated in the same way. Thus, assays with detection and quantitation ability for chemokine RNA expression will be highly relevant to the overall assessment of patient immunocompetence.

We claim:

1. A method for the detection of quantitation of MDC RNA in a sample, comprising:
   a) obtaining a sample which may contain MDC RNA;
   b) performing an isothermal transcription based amplification on the sample with two primers, a first primer being about 15–26 nucleotides in length and comprising at least 10 consecutive nucleotides of a sequence selected from the group consisting of SEQ ID NO:2 and SEQ ID NO:3, and a second primer being about 15–26 nucleotides in length and comprising at least 10 consecutive nucleotides of a sequence selected from the group consisting of SEQ ID NO:6 and SEQ ID NO:7; and
   c) detecting the amplification product using at least one probe, whereby detection of the amplification product indicates the presence and/or quantity of MDC RNA in the sample.

2. The method of claim 1, wherein the sample comprises cells and RNA is extracted from the cells in the sample prior to step b).

3. The method of claim 1, wherein the detection step uses a labelled probe, wherein the labelled probe comprises a sequence selected from the group consisting of SEQ ID NO:9, and SEQ ID NO:10, whereby hybridization of the probe to the amplification product indicates the presence and/or quantity of MDC RNA in the sample.

4. The method of claim 1, wherein the at least one probe comprises SEQ ID NO:8, SEQ ID NO:9 and SEQ ID NO:10.

5. The method of claim 1, wherein the at least one probe comprises a wild type probe selected from the group consisting of SEQ ID NO:8 and SEQ ID NO:9.

6. The method of claim 5, further comprising adding a known amount of control RNA Q at step b), and detecting amplification product of Q by using a labeled probe comprising the sequence of SEQ ID NO:10, whereby the quantity of MDC RNA in the sample is calculated by comparing the signals of the probes for Q and the wild-type probe.

7. The method of claim 1, wherein said first primer further comprises an RNA polymerase promoter sequence covalently bonded to the 5' end thereof.

8. The method of claim 7, wherein said RNA polymerase promoter sequence is a T7 RNA polymerase promoter sequence as set forth in SEQ ID NO:1.

9. The method of claim 8, wherein said first primer is SEQ ID NO:4 and said second primer is SEQ ID NO:6.

10. The method of claim 9, wherein the at least one probe comprises SEQ ID NO:8, SEQ ID NO:9 and SEQ ID NO:10.

11. A kit for the detection or quantitation of MDC RNA in a sample, comprising, two primers selected from the group consisting of SEQ ID NO:2, SEQ ID NO:3, SEQ ID NO:4, SEQ ID NO:5, SEQ ID NO:6, and SEQ ID NO:7.

12. The kit of claim 11, wherein the primers are SEQ ID NO:4 and SEQ ID NO:6.

13. The kit of claim 11, wherein the primers are SEQ ID NO:4 and SEQ ID NO:7.

14. The kit of claim 11, wherein the primers are SEQ ID NO:5 and SEQ ID NO:6.

15. The kit of claim 11, wherein the primers are SEQ ID NO:5 and SEQ ID NO:7.

16. The kit of claim 11, further comprising at least one probe comprising a sequence selected from the group consisting of SEQ ID NO:8, SEQ ID NO:9, and SEQ ID NO;10.

17. An oligonucleotide selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9 and SEQ ID NO:10.

18. An oligonucleotide of about 15–26 nucleotides, comprising at least 10 consecutive nucleotides of a sequence selected from the group consisting of SEQ ID NO:2, SEQ ID NO:3, SEQ ID NO:6, and SEQ ID NO:7.

19. An oligonucleotide of about 15–26 nucleotides, comprising at least 10 consecutive nucleotides of a sequence selected from the group consisting of SEQ ID NO:2 and SEQ ID NO:3, further comprising an RNA polymerase promoter sequence covalently bonded to the 5' end thereof.

20. The oligonucleotide of claim 19, wherein the RNA polymerase promoter sequence is a T7 RNA polymerase promoter sequence as set forth in SEQ ID NO:1.

21. An oligonucleotide selected from the group consisting of SEQ ID NO:2, SEQ ID NO:3, SEQ ID NO:4, SEQ ID NO:5, SEQ ID NO:6, and SEQ ID NO:7.

22. A pair of oligonucleotides for the detection or quantitation of MDC RNA, a first oligonucleotide of said pair being about 15–26 nucleotides in length and comprising at least 10 consecutive nucleotides of a sequence selected from the group consisting of SEQ ID NO:2 and SEQ ID NO:3, and a second oligonucleotide of said pair being about 15–26 nucleotides in length and comprising at least 10 consecutive nucleotides of a sequence selected from the group consisting of SEQ ID NO:6 and SEQ ID NO:7.

23. The pair of oligonucleotides of claim 22, wherein said first oligonucleotide is selected from the group consisting of SEQ ID NO:2 and SEQ ID NO:3, and said second oligonucleotide is selected from the group consisting of SEQ ID NO:6 and SEQ ID NO:7.

24. The pair of oligonucleotides of claim 22, wherein said first oligonucleotide further comprises an RNA polymerase promoter sequence covalently bonded to the 5' end thereof.

25. The pair of oligonucleotides of claim 24, wherein the RNA polymerase promoter sequence is a T7 RNA polymerase promoter sequence as set forth in SEQ ID NO:1.

26. A kit for the detection or quantitation of MDC RNA in a sample, comprising the pair of oligonucleotides of claim 22.

27. The kit of claim 26, further comprising at least one probe comprising a sequence selected from the group consisting of SEQ ID NO:8, SEQ ID NO:9, and SEQ ID NO:10.

* * * * *

UNITED STATES PATENT AND TRADEMARK OFFICE
CERTIFICATE OF CORRECTION

PATENT NO : 6,093,542
DATED : July 25, 2000
INVENTOR(S) : ROMANO ET AL.

It is certified that error appears in the above-identified patent, and that said Letters Patent is hereby corrected as shown below:

Please correct line 1 of claim 1 by replacing "detection of quantitation" with -- detection or quantitation --.

Signed and Sealed this

Seventeenth Day of April, 2001

*Attest:*

NICHOLAS P. GODICI

*Attesting Officer*     *Acting Director of the United States Patent and Trademark Office*